US009445726B2

(12) United States Patent
Toriumi et al.

(10) Patent No.: US 9,445,726 B2
(45) Date of Patent: Sep. 20, 2016

(54) ELECTRONIC APPARATUS, THERMOMETER, BODY TEMPERATURE MANAGEMENT SYSTEM, ALARM CONTROL METHOD, AND PROGRAM

(71) Applicant: Rakuten, Inc., Shinagawa-ku, Tokyo (JP)

(72) Inventors: Satoko Toriumi, Shinagawa-ku (JP); Fumie Suzuki, Shinagawa-ku (JP)

(73) Assignee: Rakuten, Inc., Tokyo (JP)

( * ) Notice: Subject to any disclaimer, the term of this patent is extended or adjusted under 35 U.S.C. 154(b) by 0 days.

(21) Appl. No.: 14/370,557

(22) PCT Filed: Mar. 28, 2013

(86) PCT No.: PCT/JP2013/059259
§ 371 (c)(1),
(2) Date: Jul. 3, 2014

(87) PCT Pub. No.: WO2014/155605
PCT Pub. Date: Oct. 2, 2014

(65) Prior Publication Data
US 2015/0289768 A1    Oct. 15, 2015

(51) Int. Cl.
*G08B 17/00* (2006.01)
*A61B 5/01* (2006.01)
*G01K 13/00* (2006.01)
*A61B 5/00* (2006.01)
*G01K 1/02* (2006.01)

(52) U.S. Cl.
CPC ................. *A61B 5/01* (2013.01); *A61B 5/746* (2013.01); *G01K 1/022* (2013.01); *G01K 13/002* (2013.01)

(58) Field of Classification Search
CPC ....................................................... G06F 3/041
See application file for complete search history.

(56) References Cited

U.S. PATENT DOCUMENTS

| 5,253,230 A | * 10/1993 | Kuo ...................... G04C 21/02 368/243 |
| 6,882,334 B1 | * 4/2005 | Meyer ................... G06F 3/0231 340/6.1 |
| 2003/0210146 A1 | * 11/2003 | Tseng ..................... G01K 1/024 340/573.1 |
| 2003/0212311 A1 | * 11/2003 | Nova .................. A61N 1/37258 600/300 |
| 2008/0259742 A1 | 10/2008 | Tadanori |
| 2010/0152606 A1 | 6/2010 | Menashe |
| 2011/0190579 A1 | * 8/2011 | Ziarno ............... A61B 1/00016 600/109 |
| 2012/0238900 A1 | * 9/2012 | Rechberg ................. A61B 5/01 600/549 |

(Continued)

FOREIGN PATENT DOCUMENTS

| CN | 202836774 U | 3/2013 |
| JP | 3028311 U | 9/1996 |

(Continued)

OTHER PUBLICATIONS

English Translation of International Search Report of PCT/JP2013/059259 dated May 21, 2013.

(Continued)

*Primary Examiner* — Omeed Alizada
(74) *Attorney, Agent, or Firm* — Sughrue Mion, PLLC

(57) ABSTRACT

An electronic apparatus includes an alarm unit, a reception unit, and a control unit. The alarm unit is capable of outputting an alarm. The reception unit receives an alarm stop signal from a thermometer. The control unit causes the alarm unit to output the alarm at a set time and stop the alarm on the basis of the alarm stop signal.

13 Claims, 8 Drawing Sheets

(56) References Cited

U.S. PATENT DOCUMENTS

2012/0265032 A1* 10/2012 Ben-David .............. A61B 5/01
                                                    600/301
2013/0243418 A1* 9/2013 Haramaty ............ H04B 10/032
                                                      398/5

FOREIGN PATENT DOCUMENTS

| JP | 09-89676 A | 4/1997 |
|---|---|---|
| JP | 10-281891 A | 10/1998 |
| JP | 2010-167043 A | 8/2010 |
| TW | 200842531 A | 11/2008 |
| TW | 201237575 A | 9/2012 |

OTHER PUBLICATIONS

International Search Report and Written Opinion of the International Searching Authority for PCT/JP2013/059259 dated May 21, 2013.

* cited by examiner

| Fortune-telling result | Sectioned period | Presentation pattern |
|---|---|---|
| A | 1 | A-1 |
| | 2 | A-2 |
| | 3 | A-3 |
| | 4 | A-4 |
| B | 1 | B-1 |
| | 2 | B-2 |
| | 3 | B-3 |
| | 4 | B-4 |
| ⋮ | ⋮ | ⋮ |

FIG.10

_ELECTRONIC APPARATUS,
THERMOMETER, BODY TEMPERATURE
MANAGEMENT SYSTEM, ALARM
CONTROL METHOD, AND PROGRAM_

TECHNICAL FIELD

The present invention relates to an electronic apparatus, a thermometer, a body temperature management system, an alarm control method, and a program.

BACKGROUND ART

Conventionally, basal thermometers capable of measuring basal body temperatures of women are known (see, Patent Document 1). Basal body temperatures each show such a biphasic form that a high-temperature phase and a low-temperature phase are periodically repeated, which is caused by a hormonal secretion condition. That is, women can grasp their body conditions resulting from hormonal secretion conditions by regularly taking basal body temperatures. Thus, in recent years, basal body temperature data has been positively used for not only control of pregnancy, contraception, or the like but also health management such as a diet.

On the other hand, to obtain highly reliable basal body temperature data, it is necessary to take a basal body temperature at about the same time every day. Therefore, there is a problem in that highly reliable basal body temperature data cannot be obtained in the case where taking the basal body temperature is forgotten or performed at considerably different times. In view of this, for example, Patent Document 1 discloses a basal thermometer having an alarm function.

Patent Document 1: Japanese Patent Application Laid-open No. HEI10-281891

SUMMARY OF INVENTION

Problem to be Solved by the Invention

However, a basal thermometer is urged to be compact, so a simple apparatus structure is desired, and a space for a display unit or the like is limited. For this reason, there is a limit to provide a basal thermometer with a multifunctional alarm apparatus having a snooze function or the like, for which an input operation of setting an alarm clock or the like is easily performed.

Further, in the case where an apparatus different from the thermometer is provided with the alarm function, there is a problem in that an operation of stopping the alarm and an operation of starting a measurement of a body temperature are not linked, and it is impossible to urge habitual measurement of the body temperature.

In view of the circumstances as described above, an object of the present invention is to provide an electronic apparatus, a thermometer, a body temperature management system including these, an alarm control method, and a program which are capable of urging the habitual measurement of the body temperature and increasing reliability of basal body temperature data.

Means for Solving the Problem

To solve the problem mentioned above, an electronic apparatus according to an embodiment of the present invention includes an alarm unit, a reception unit, and a control unit.

The alarm unit is capable of outputting an alarm.

The reception unit receives an alarm stop signal from a thermometer.

The control unit causes the alarm unit to output the alarm at a set time and stop the alarm on the basis of the alarm stop signal.

The electronic apparatus can stop the alarm on the basis of an operation of starting a body temperature measurement with respect to a thermometer of a user, an operation of stopping the alarm, or the like. Thus, it is possible to cause the user to inevitably operate the thermometer. As a result, it is possible to urge the user to habitually take the body temperature and obtain data of highly reliable basal body temperatures or the like.

The reception unit is capable of receiving a first alarm stop signal and a second alarm stop signal from the thermometer.

When the reception unit receives the first alarm stop signal, the control unit may cause the alarm of the alarm unit to be completely stopped, and when the reception unit receives the second alarm stop signal, the control unit may cause the alarm to be temporarily stopped in such a manner that the alarm of the alarm unit is caused to be output again after a lapse of a predetermined time period.

As a result, it is possible to prevent the user from going back to sleep and urge the user to wake up reliably. In addition, even when the alarm is temporarily stopped, it is possible to urge the user to take the body temperature.

The reception unit may have a first state in which the alarm stop signal is capable of being received and a second state in which a reception of the alarm stop signal is rejected.

The control unit may cause the reception unit to shift from the second state to the first state at the set time.

As a result, it is possible to limit a time period during which the reception unit is in a standby state and contribute to a reduction in power consumption of the electronic apparatus. Further, it is possible to perform switching of the reception unit automatically, which can increase convenience of the user.

After receiving the alarm stop signal, the reception unit may receive basal body temperature data output from the thermometer when a predetermined measurement time period of the thermometer elapses.

As a result, it is possible to manage the basal body temperature data by the electronic apparatus or a server or the like connected to the electronic apparatus, which makes it possible to provide a content or a service with the use of the basal body temperature data, for example. Further, it is possible to save the user the trouble of manually transmitting the basal body temperature data, which can increase the convenience of the user.

Further, in the case where the control unit determines that the basal body temperature data is not received when the predetermined measurement time period elapses after receiving the alarm stop signal, the control unit causes the alarm to be output again.

As a result, it is possible to prevent the user from falling asleep after stopping the alarm and reliably cause the user to take the body temperature.

Further, the electronic apparatus may further include a storage unit that stores a plurality of presentation patterns of a predetermined content.

The control unit may select and reproduce the presentation pattern corresponding to the basal body temperature data received from among the plurality of presentation patterns of the predetermined content.

As a result, it is possible to provide enjoyment to the user at the time of or after the measurement. Thus, it is possible to prevent the user from going back to sleep after the measurement and motivate the user to continue the measurement.

Further, the reception unit may be capable of receiving data relating to a change over time in body temperature measurement value from the thermometer.

The control unit may determine whether a user falls asleep or not during a body temperature measurement on the basis of the change over time in the body temperature measurement value received, and in the case where the control unit determines that the user falls asleep, the control unit may cause the alarm to be output.

As a result, it is possible to determine whether the user falls asleep or not by using the body temperature measurement value naturally obtained at the time of the measurement of the body temperature. Therefore, it is possible to urge the user to wake up without requiring another structure. Further, an unnecessarily long measurement of the body temperature is avoided, which can contribute to a reduction in power consumption of a battery of the thermometer.

A thermometer according to an embodiment of the present invention includes a communication unit that outputs a signal for stopping an alarm of an electronic apparatus having an alarm function.

With this structure, it is possible to manage a measurement time of the body temperature and increase reliability of data such as the basal body temperature. In addition, it is possible to provide the alarm function to the electronic apparatus independent of the thermometer, which can make the thermometer more compact.

The thermometer may further include an operation reception unit that receives an input operation of a user and a control unit that generates the signal on the basis of the input operation from the operation reception unit.

With this structure, the user can reliably operate the thermometer at the time of awakening.

In the thermometer, when the signal is generated, a measurement of a body temperature may be started.

With this structure, the operation of stopping the alarm also serves as the operation of stating the measurement, which can reliably cause the user to take the body temperature. Thus, it is possible to increase the reliability of the data such as the basal body temperature.

Further, the thermometer may further include a casing having a front surface, a back surface, and a side surface. The front surface includes a display unit on which a body temperature value measured is displayed. The back surface is opposed to the front surface. The side surface is continuously connected with the front surface and the back surface and capable of being held by the user during the measurement of the body temperature.

The operation reception unit may be disposed on the side surface.

With this structure, the operation reception unit is disposed on a part which is held by the user. Thus, the user can smoothly take the body temperature without holding the thermometer again after the operation of stopping the alarm.

The operation reception unit may be capable of receiving a first input operation and a second input operation different from the first input operation.

The control unit may generate a first alarm stop signal for completely stopping the alarm on the basis of the first input operation and generate a second alarm stop signal for temporarily stopping the alarm in such a manner that the alarm is generated again after a lapse of a predetermined time period on the basis of the second input operation.

Further, the communication unit may be capable of outputting measured basal body temperature data when a predetermined measurement time period elapses.

With this structure, it is possible to save the trouble of transmitting the basal body temperature data by the user, which can increase convenience of the user. Further, it is possible to automatically transmit the basal body temperature data immediately after the measurement or the like and thus update the information processing apparatus or the like that manages the data with the latest basal body temperature data. Therefore, when a content or a service that uses the basal body temperature data is provided, these can be provided on the basis of the highly reliable data.

A body temperature management system according to an embodiment of the present invention includes a thermometer and an electronic apparatus.

The thermometer is capable outputting an alarm stop signal.

The electronic apparatus includes an alarm unit, a reception unit, and a control unit.

The alarm unit is capable of outputting an alarm.

The reception unit receives the alarm stop signal from the thermometer.

The control unit causes the alarm unit to output the alarm at a set time and stop the alarm on the basis of the alarm stop signal.

An alarm control method according to an embodiment of the present invention includes a step of causing an alarm for urging a user to wake up to be output at a set time.

An alarm stop signal is received from a thermometer that measures a body temperature of the user.

The alarm is caused to be stopped on the basis of the alarm stop signal.

Further, a program according to an embodiment of the present invention causes an information processing apparatus to execute the steps of causing an alarm to be output, receiving an alarm stop signal, and causing the alarm to be stopped.

In the step of causing the alarm to be output, the alarm for urging a user to wake up is output at a set time.

In the step of receiving the alarm stop signal, the alarm stop signal is received from a thermometer that measures a body temperature of the user.

In the step of causing the alarm to be stopped, the alarm is caused to be stopped on the basis of the alarm stop signal.

Effect of the Invention

As described above, according to the present invention, it is possible to provide the electronic apparatus, the thermometer, the body temperature management system including these, and the alarm control method, and the program capable of urging the habitual measurement of the body temperature to increase the reliability of the basal body temperature data.

BRIEF DESCRIPTION OF DRAWINGS

FIG. 10 A diagram showing a specific example of a database stored in the user terminal in the fourth embodiment of the present invention.

BEST MODE(S) FOR CARRYING OUT THE INVENTION

Hereinafter, embodiments of the present invention will be described with reference to the drawings.

<First Embodiment>

First, a first embodiment of the present invention will be described.

[Outline of Body Temperature Management System]

Figure 1:
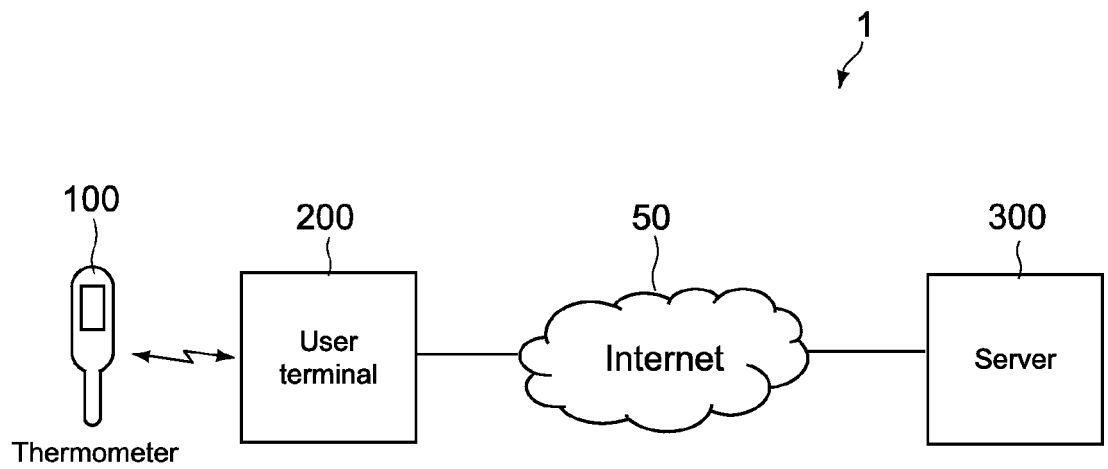
FIG. 1 A diagram showing a network structure of a body temperature management system according to a first embodiment of the present invention.

FIG. 1 is a diagram showing a schematic structure of a body temperature management system according to this embodiment.

As shown in the figure, a body temperature management system 1 includes a thermometer 100, a user terminal (electronic apparatus) 200, and a server 300 on an Internet 50.

The thermometer 100 is an electronic thermometer capable of measuring a basal body temperature of a user and causing an alarm of the user terminal 200 to be stopped by a user operation. In this embodiment, in the case where the user terminal 200 is set to a snooze mode, an input operation corresponding to a complete stop and an input operation corresponding to a temporary stop by the snooze function can be performed for the thermometer 100.

Further, as a measurement method, the thermometer 100 adopts a prediction/actual measurement method, by which both of a prediction body temperature check and an actual measurement body temperature check can be performed. The thermometer 100 uses the structure in which an intraoral temperature close to a deep body temperature is measured, but the structure is not limited to this. For example, the structure may be used in which a body temperature on an armpit, an ear, or the like can be measured.

Furthermore, the thermometer 100 can automatically transmit measured basal body temperature data to the user terminal 200 when a prediction time period elapses during which a prediction body temperature check is performed. It should be noted that the "when . . . elapses" is not strictly limited to the elapsed time but has an idea including a range after the prediction time period elapses until several seconds pass.

It should be noted that the "snooze function" refers to such a function that an alarm is temporarily stopped, and then an alarm is generated again after a predetermined time period elapses. In addition, the "snooze mode" refers to a mode in which the snooze function can be exerted in the user terminal 200.

The user terminal 200 is an electronic apparatus having an alarm function and can specifically be an information processing apparatus such as a smart phone, a mobile phone, a personal computer, a tablet, and a mobile game machine connectable with the Internet 50.

The user terminal 200 stops the alarm by a user operation with respect to the thermometer 100. In this embodiment, when the user terminal 200 is in the snooze mode, the user terminal 200 can perform a complete stop and a temporary stop by the snooze function on the basis of the user operation with respect to the thermometer 100.

Further, the user terminal 200 accesses the server 300 via the Internet 50 and uploads the basal body temperature data received from the thermometer 100 to the server 300. Furthermore, the user terminal 200 receives and reproduces analysis data of the basal body temperatures processed by the server 300.

The server 300 can provide, to the user terminal 200, a body temperature management application with an alarm function at the time of a body temperature measurement and a management function of the basal body temperatures. Further, the server 300 can perform an analysis process of the basal body temperature data received from the user terminal 200 and transmit a graph, an advice, or the like as an analysis result thereof to the user terminal 200.

[External Structure of Thermometer]

Figure 2:
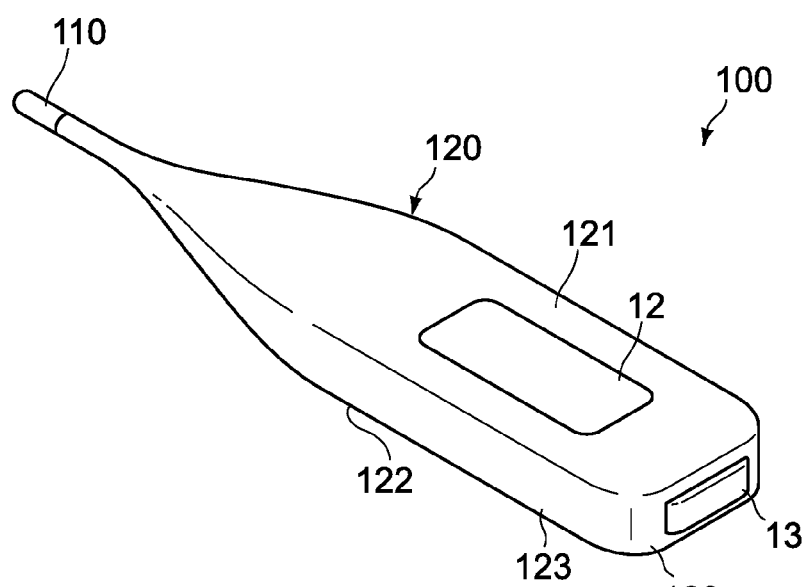
FIG. 2 A diagram showing an external structure of a thermometer in the first embodiment of the present invention.

FIG. 2 is a diagram showing an external structure of the thermometer 100. As shown in the figure, the thermometer 100 includes a temperature sensing unit 110 capable of being brought into contact with an inside of an oral cavity of a user and a casing 120. The temperature sensing unit 110 is formed as a metal cap disposed at a tip of the casing 120 and collects and transmits heat to a measurement unit 10 to be described later.

The casing 120 includes a front surface 121, a back surface 122 opposed to the front surface, and a side surface 123.

On the front surface 121, a display unit 12 that displays a body temperature value is disposed.

The back surface 122 is a surface opposed to the front surface 121.

The side surface 123 is a surface in continuous connection with the front surface 121 and the back surface 122 and can be held by the user during a body temperature measurement. On the side surface 123, an operation reception unit 13 to be described later is disposed. The side surface 123 may include a plurality of surfaces as exemplified in FIG. 2 or may be formed of one curved surface.

Next, a hardware structure of the thermometer 100 will be described.

[Hardware Structure of Thermometer]

Figure 3:
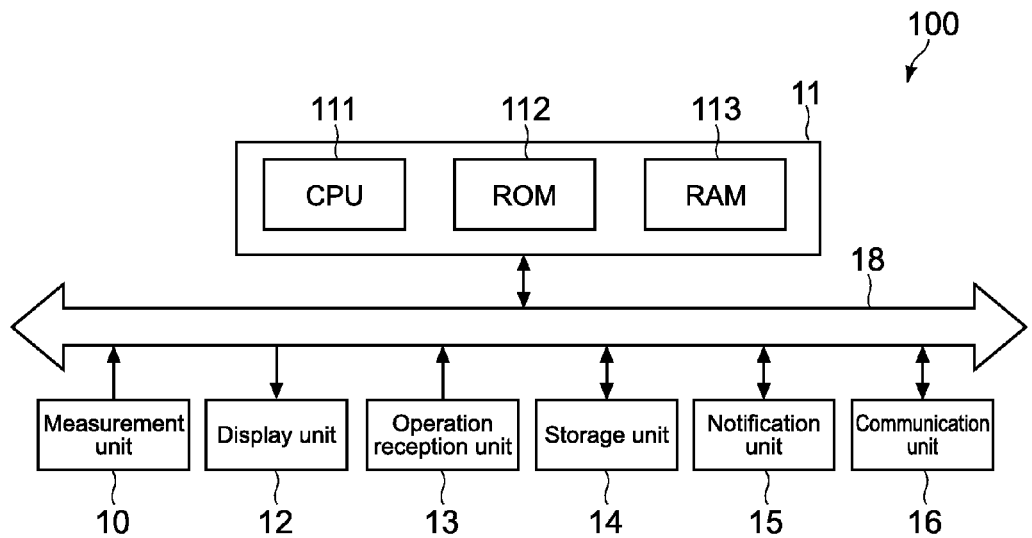
FIG. 3 A block diagram showing a hardware structure of the thermometer in the first embodiment of the present invention.

FIG. 3 is a diagram showing the hardware structure of the thermometer 100. As shown in the figure, the thermometer 100 is provided with the measurement unit 10, a control unit 11, the display unit 12, the operation reception unit 13, a storage unit 14, a notification unit 15, a communication unit 16, and a bus 18 that connects these with one another.

The measurement unit 10 is configured as a temperature sensor capable of converting a change in body temperature (basal body temperature) of the user into an electrical signal. Specifically, the measurement unit 10 can adopt a semiconductor-type temperature sensor with a temperature resolution of 0.05° C. in a range of 35° C. to 38° C. The measurement unit 10 is disposed in the temperature sensing unit 110, for example.

The control unit 11 includes a CPU (Central Processing Unit) 111, a ROM (Read Only Memory) 112, and a RAM (Random Access Memory) 113.

The CPU 111 accesses the RAM 113 or the like when necessary and performs overall control of all blocks of the thermometer 100 while performing various operation processes. The ROM 112 is a nonvolatile memory in which firmware such as a program for calculating a body temperature value executed by the CPU 111 is fixedly stored. The RAM 113 is used as a work area or the like for the CPU 111 and temporarily stores various pieces of data in processing.

In this embodiment, the CPU 111 calculates the basal body temperature value from an electrical signal relating to the change in body temperature obtained by the measurement unit 10, outputs the basal body temperature value to the display unit 12, and outputs basal body temperature data to the communication unit 16. The CPU 111 calculates the basal body temperature value by a method corresponding to each of the measurement methods of the prediction body temperature check and the actual measurement body temperature check. For example, in the case where only the prediction body temperature check is performed, the CPU 111 calculates the basal body temperature value by a predetermined algorism from a change over time in the electrical signal obtained during the prediction time period. In the case where the actual measurement body temperature check is performed subsequently to the prediction body temperature check, a basal body temperature value (actual measurement value) corresponding to the electrical signal obtained after the actual measurement time period elapses is calculated.

It should be noted that in this embodiment, the "basal body temperature data" refers to data obtained by relating the calculated basal body temperature values to measurement dates and times.

Further, on the basis of an input operation from the operation reception unit 13, the CPU 111 generates an alarm stop signal for stopping the alarm. In this embodiment, the CPU 111 generates, as the alarm stop signal, a complete stop signal (first alarm stop signal) and a snooze stop signal (second stop signal). The complete stop signal is generated on the basis of a first input operation of the operation reception unit 13 and completely stops the alarm generated from the user terminal 200. The snooze stop signal is generated on the basis of a second input operation of the operation reception unit 13 and temporarily stops the alarm generated from the user terminal 200 in such a manner that the alarm is generated again after a predetermined time period elapses.

The display unit 12 is a display device that uses an LCD (Liquid Crystal Display) or the like and displays the basal body temperature value or the like calculated by the CPU 111.

The operation reception unit 13 is formed of an operation button or the like and receives an input operation by the user with respect to the thermometer 100. Specifically, the operation reception unit 13 can receive an input operation of stopping the alarm of the user terminal 200, an input operation of giving an instruction to start and stop the thermometer 100 (turn on and off the power), or the like. In the case where the operation reception unit 13 is formed of the operation button, the number of operation buttons may be one or more. In the case of one, the button related to stopping the alarm may double as a start/stop button of the thermometer 100.

Further, in this embodiment, the operation reception unit 13 receives the first input operation of completely stopping the alarm and the second input operation of temporarily stopping the alarm by the snooze function. The first input operation may be a so-called holding-down operation for two seconds or more, for example. The second input operation may be a pressing operation for a short time period of two second or less, for example.

In this embodiment, the operation reception unit 13 is disposed on the side surface 123 of the casing 120, which is capable of being held by the user at the time of the measurement (see, FIG. 2). With this structure, after the user operates the operation reception unit 13, the user can take a body temperature while holding the thermometer 100 without change.

The storage unit 14 is a nonvolatile memory such as a flash memory (SSD; Solid State Drive) and another solid-state memory. In the storage unit 14, the measured basal body temperature value of the user and the measurement date and time are stored with the basal body temperature value and the measurement date and time associated with each other.

The notification unit 15 is formed of a speaker or the like that generates beeps, for example. The notification unit 15 notifies the user of termination of the body temperature measurement or the like with the beeps. It should be noted that sounds generated by the notification unit 15 are not limited to the beeps but may be music or voice.

The communication unit 16 is formed by a communication module capable of being connected with the user terminal 200 in a wired or wireless manner. The communication unit 16 can adopt, as a communication system, a machine-to-machine communication such as Bluetooth (registered trademark), NFC (Near Field Communication), and infrared communication.

[Hardware Structure of User Terminal]

Figure 4:
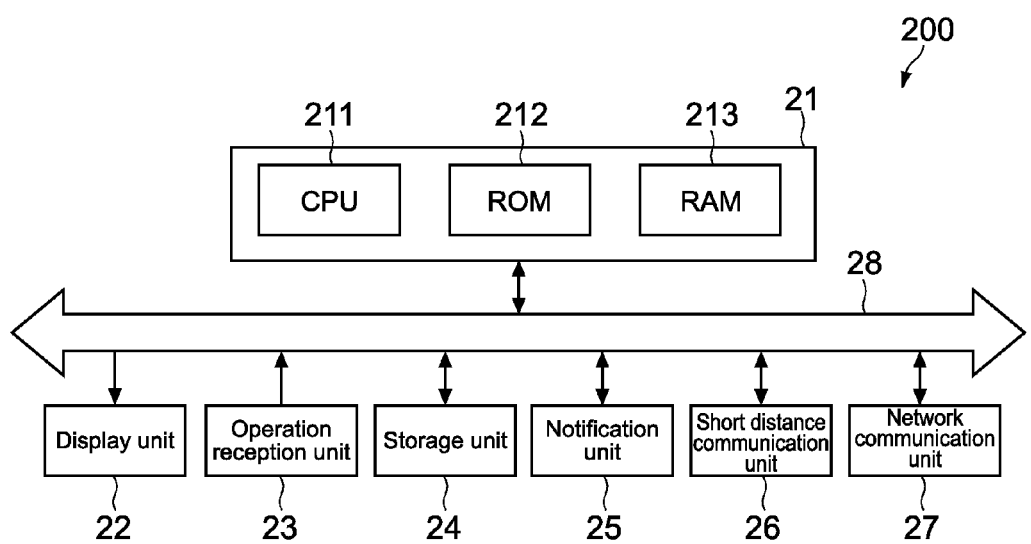
FIG. 4 A block diagram showing a hardware structure of a user terminal (electronic apparatus) in the first embodiment of the present invention.

FIG. 4 is a diagram showing a hardware structure of the user terminal 200. As shown in the figure, the user terminal 200 is provided with a control unit 21, a display unit 22, an operation reception unit 23, a storage unit 24, a notification unit (alarm unit) 25, a short distance communication unit (reception unit) 26, a network communication unit 27, and a bus 28 that connects these with one another. The display unit 22, the operation reception unit 23, the storage unit 24, the notification unit 25, the short distance communication unit 26, the network communication unit 27, and the like are connected to the bus 28 through an input and output interface (not shown).

The control unit 21 includes a CPU 211, a ROM 212, and a RAM 213.

The CPU 211 accesses the RAM 213 or the like when necessary and performs overall control of all blocks of the user terminal 200 while performing various operation processes. The ROM 212 is a nonvolatile memory in which an OS and firmware such as a program and various parameters executed by the CPU 211 are fixedly stored. The RAM 213 is used as a work area or the like for the CPU 211 and temporarily stores the OS, various applications in execution, and various pieces of data in processing.

The display unit 22 is a display device that uses an LCD, an OELD (Organic Electroluminescence Display), or the like.

The operation reception unit 23 is an input apparatus such as a keyboard and a touch panel. In the case where the operation reception unit 23 is the touch panel, the touch panel may be integrally formed with the display unit 22.

The storage unit 24 is a nonvolatile memory such as an HDD (Hard Disk Drive), a flash memory (SSD), and another solid-state memory. In the storage unit 24, the OS, the various applications, and the various pieces of data are stored.

In the storage unit 24, a body temperature management application including an alarm control program is stored. The body temperature management application is provided with an alarm function executed by the CPU 211 in accordance with the alarm control program and a function of presenting various prediction dates analyzed by the server 300, a graph showing a body condition or the like, an advice based on the analysis result, or the like.

As a method of installing the body temperature management application, the application may be downloaded from the server 300 through the network communication unit 27, or the application recorded in a recording medium such as a CD (Compact Disc) and a DVD (Digital Versatile Disc) may be installed through a drive (not shown) or the like of the user terminal 200. Alternatively, the application may be preinstalled in the user terminal 200.

The notification unit 25 is formed of a speaker, a vibrator that generates vibrations, or the like. Further, in this embodiment, the notification unit 25 functions as an alarm unit.

The short distance communication unit 26 is formed of a communication module which can be connected with the thermometer 100 in a wired or wireless manner. The short distance communication unit 26 functions as a "reception unit" in this embodiment. The short distance communication unit 26 can adopt a wireless machine-to-machine communication such as Bluetooth (registered trademark), NFC, and infrared communication as a communication system.

In this embodiment, the short distance communication unit 26 has a reception standby state (first state) in which it is possible to receive the alarm stop signal from the thermometer 100 and a reception rejection state (second state) in which the reception of the alarm stop signal is rejected. The short distance communication unit 26 is kept to be in the reception rejection state when the user terminal 200 does not exert the alarm function, but at an alarm set time, the short distance communication unit 26 is shifted to the reception standby state by the control unit 21, with the result that the alarm stop signal can be received.

Further, the short distance communication unit 26 can receive first and second alarm stop signals as the alarm stop signal.

The network communication unit 27 is formed of a communication module that can be connected to the Internet 50 in a wired or wireless manner and performs communication processing with the server 300. The network communication unit 27 accesses the server 300 via the Internet 50 and uploads the basal body temperature data received from the thermometer 100 to the server 300. It should be noted that, to the basal body temperature data uploaded to the server 300, for example, a user ID or the like for identifying the user is added.

[Hardware Structure of Server]

Figure 5:
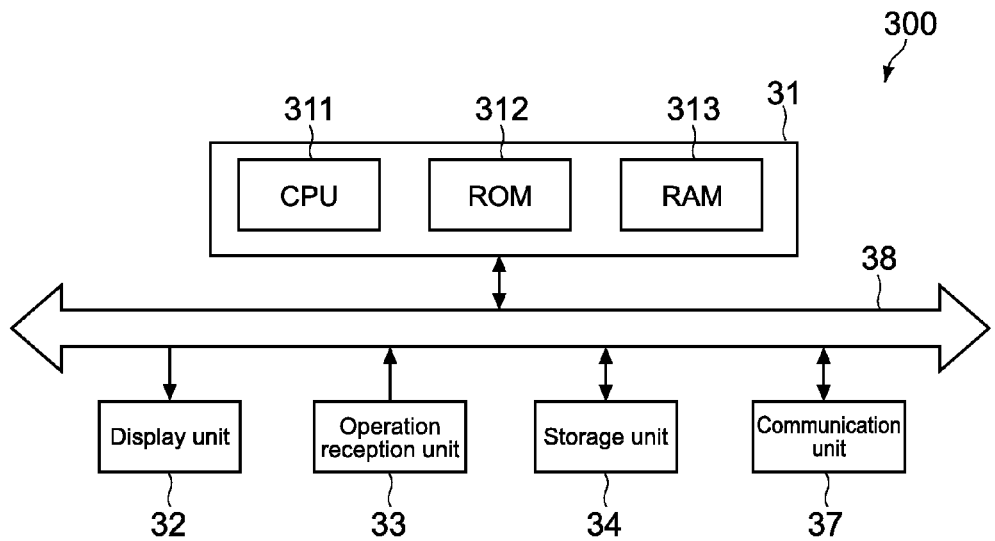
FIG. 5 A block diagram showing a hardware structure of a server in the first embodiment of the present invention.

FIG. 5 is a diagram showing a hardware structure of the server 300. As shown in the figure, the server 300 is provided with a control unit 31, a display unit 32, an operation reception unit 33, a storage unit 34, a communication unit 37, and a bus 38 that connects these with one another. The display unit 32, the operation reception unit 33, the storage unit 34, the communication unit 37, and the like are connected to the bus 38 through an input and output interface (not shown).

The control unit 31 includes a CPU 311, a ROM 312, and a RAM 313.

The CPU 311 accesses the RAM 313 or the like when necessary and performs overall control of all blocks of the server 300 while performing various operation processes. The ROM 312 is a nonvolatile memory in which an OS and firmware such as a program and various parameters executed by the CPU 311 are fixedly stored. The RAM 313 is used as a work area or the like for the CPU 311 and temporarily stores the OS, various applications in execution, and various pieces of data in processing.

Further, the CPU 311 may perform an analysis process for the basal body temperature data received from the user terminal 200 in accordance with a basal body temperature data analysis program stored in the storage unit 34. For example, the CPU 311 performs the analysis process for the basal body temperature data, thereby calculating the next ovulation prediction date and menstruation start prediction date. Further, on the basis of these calculation results, the CPU 311 may section a predetermined period for each body condition or the like of the user.

The CPU 311 generates analysis data that indicates analysis results of the ovulation prediction date, the menstruation start prediction date, the body condition, or the like. The analysis data may be provided by indicating the analysis results on a calendar or a graph.

The display unit 32 is a display device that uses an LCD, an OELD, a CRT (Cathode Ray Tube), or the like.

The operation reception unit 33 is, for example, a pointing device such as a mouse, a keyboard, a touch panel, or another input apparatus. In the case where the operation reception unit 33 is the touch panel, the touch panel can be integrally formed with the display unit 32.

The storage unit 34 is a nonvolatile memory such as an HDD, a flash memory (SSD), and another solid-state memory. In the storage unit 34, the OS, the various applications, and the various pieces of data are stored.

In the storage unit 34, a basal body temperature data analysis program is stored. Further, the storage unit 34 stores analysis data that indicates analysis results of the basal body temperature data of each user which is transmitted from the user terminal 200 and the basal body temperature data of each user which is processed by the control unit 31. In addition, these pieces of data are associated with the user IDs or the like and stored for each user.

The communication unit 37 is an NIC or the like for connection to the Internet 50 and performs a communication process with the user terminal 200 or the like. Upon request of the user terminal 200, the communication unit 37 transmits the basal body temperature analysis data processed by the control unit 31 (CPU 311) to the user terminal 200 via the Internet 50. Further, the analysis data may include an advice or the like related to the body condition created from the analysis result.

[Software Structure of User Terminal]

Figure 6:
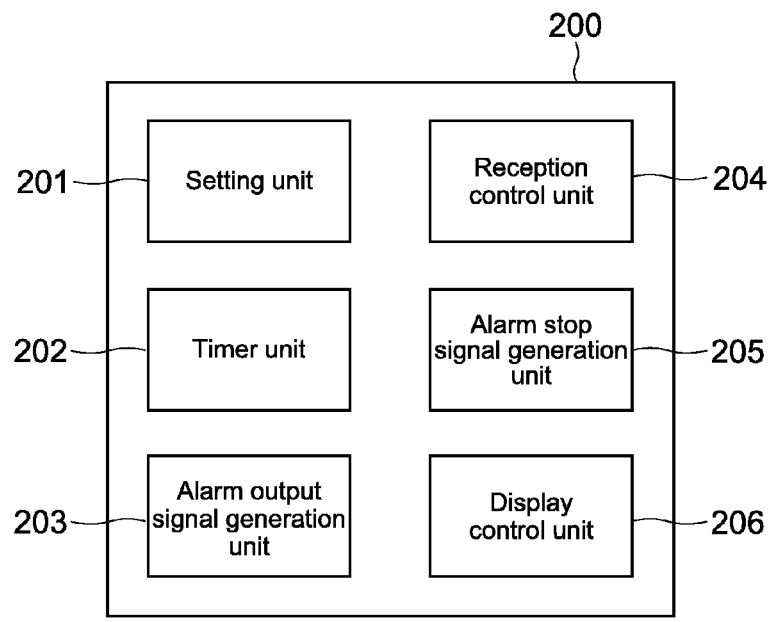
FIG. 6 A block diagram showing a software structure of the user terminal in the first embodiment of the present invention.

FIG. 6 is a function block diagram showing a software module of the user terminal 200. The software module is provided as a function of a body temperature management application capable of controlling the alarm. The body temperature management application is stored in the storage unit 24 and executed by the CPU 211 as described above.

As shown in the figure, the user terminal 200 includes a setting unit 201, a timer unit 202, an alarm output signal generation unit 203, a reception control unit 204, an alarm stop signal generation unit 205, and a display control unit 206.

The setting unit 201 receives various settings relating to the alarm through the operation reception unit 23. For example, the setting unit 201 can receive settings of an alarm set time, on and off of the snooze mode, a snooze time period, a snooze count, a duration of the alarm, and the like. When receiving the set time or the setting of the snooze time period, the setting unit 201 notifies the timer unit 202 of the set time or the like.

It should be noted that the snooze time period refers to a time period from when the temporary stop is performed by the snooze function until the alarm is generated again. Further, the snooze count refers to the number of times that the temporary stop and regeneration of the alarm can be alternated.

Further, the setting unit 201 can register a plurality of setting patterns every weekdays or holidays or for each specified day of week, for example. The contents of the various settings in the setting unit 201 are stored in the storage unit 24.

The timer unit 202 manages time in the body temperature management application. Specifically, at the alarm set time specified by the user, the timer unit 202 notifies the alarm output signal generation unit 203 of the fact. Further, in the case where the second alarm stop signal corresponding to the temporary stop by the snooze function is obtained, the timer unit 202 notifies the alarm output signal generation unit 203 of the fact again, when the snooze time period elapses after the signal is obtained.

When receiving the notification of the alarm set time from the timer unit 202, the alarm output signal generation unit 203 generates a signal for causing the alarm to be output with respect to the notification unit 25. In addition, similarly, when receiving the notification of the snooze time period from the timer unit 202, the alarm output signal generation unit 203 generates a signal for causing the alarm to be output with respect to the notification unit 25.

It should be noted that the alarm output signal generation unit 203 may output the same signal or different signals to the notification unit 25 at the time of the first alarm and at the time of the second alarm and a alarm subsequent thereto by the snooze function. In the case where the different signals are output, it is possible to cause the notification unit 25 to output the alarm with different sound patterns or the like at the first alarm and at the second alarm and an alarm subsequent thereto by the snooze function.

The reception control unit 204 controls a reception condition of the alarm stop signal in the short distance communication unit 26. For example, at the time of outputting the alarm, the reception control unit 204 can control the short distance communication unit 26 to be shifted from the reception rejection state to the reception standby state.

On the basis of the first and second alarm stop signals from the thermometer 100 which are received by the short distance communication unit 26, the alarm stop signal generation unit 205 causes the notification unit 25 to stop the alarm generated by the notification unit 25.

The display control unit 206 generates image data relating to the body temperature management application, which is to be displayed on the display unit 22. As the image data, for example, data of an alarm setting image, a graph of the analysis data of the basal body temperature, or the like can be cited.

[Operation Example of Alarm Control Process]

Subsequently, an operation example of the user terminal 200 structured as described above will be described.

Figure 7:
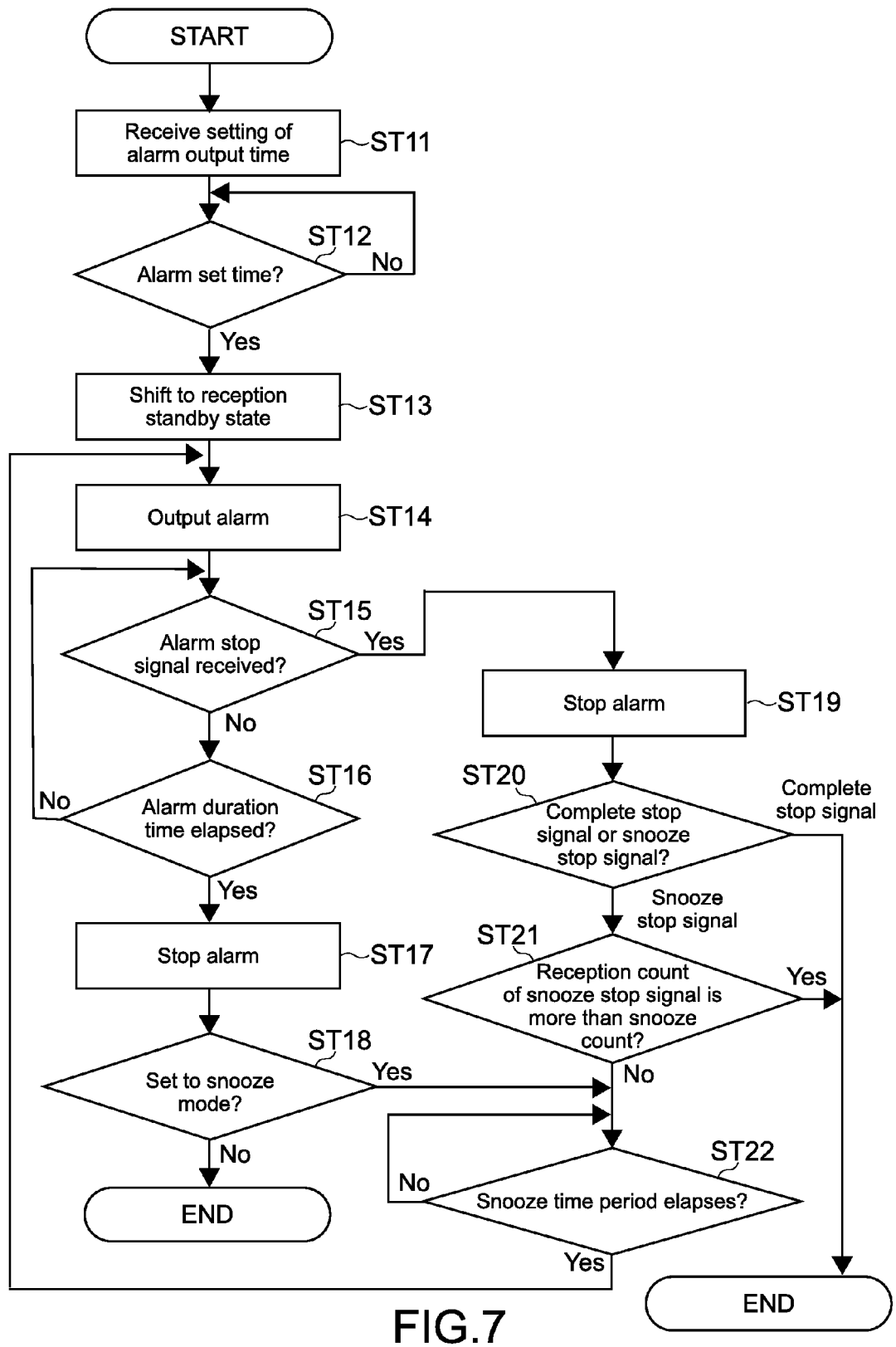
FIG. 7 A flowchart showing an operation flow of the user terminal in the first embodiment of the present invention.

FIG. 7 is a flowchart showing an operation flow of stopping the alarm when the body temperature is measured by the user terminal 200 in this embodiment. The operation is performed by different hardware and a program (software) in cooperation with each other under the control of the control unit 21 of the user terminal 200. In the following description, for convenience, the control unit 21 of the user terminal 200 is set as a main of the operation.

First, the control unit 21 receives the setting of the alarm output time on the basis of an input operation by the user (Step 11). For example, this step is performed at the time of going to sleep on a day before a day when the user is to take the basal body temperature or before that time. Further, in this step, the control unit 21 may receive the setting of the snooze mode, the alarm duration time, the snooze count, the snooze time period, or the like.

The control unit 21 determines whether the alarm set time is reached or not (Step 12). When the control unit 21 determines that the alarm set time is not reached (No in Step 12), the control unit 21 determines whether the alarm set time is reached or not again (Step 12).

When the control unit 21 determines that the alarm set time is reached (Yes in Step 12), the control unit 21 causes the short distance communication unit 26 to shift to the reception standby state (Step 13), generates the alarm output signal, and causes the notification unit 25 to output the alarm (step 14).

Then, the control unit 21 determines whether the alarm stop signal is received from the thermometer 100 or not (Step 15). When the control unit 21 determines that the signal is not received (No in Step 15), the control unit 21 determines whether the alarm duration time set by the user elapses or not (Step 16). When the control unit 21 determines that the alarm duration time does not elapse (No in Step 16), the control unit 21 determines whether the alarm stop signal is received or not, while continuing the alarm output (Step 15). When the control unit 21 determines that the alarm duration time elapses (Yes in Step 16), the control unit 21 stops the alarm (Step 17) and determines whether the mode is set to the snooze mode or not (Step 18). When the mode is not set to the snooze mode (No in step 18), the control unit 21 terminates the process.

When the mode is set to the snooze mode (Yes in Step 18), the control unit 21 proceeds to Step 22 in which whether the snooze time period elapses or not is determined.

On the other hand, when the control unit 21 determines that the alarm stop signal is received (Yes in step 15), the control unit 21 causes the alarm to be stopped (Step 19) and determines whether the alarm stop signal is a complete stop signal or a snooze stop signal (Step 20).

When the alarm stop signal is determined to be the complete stop signal ("complete stop signal" in Step 20), the control unit 21 terminates the process.

On the other hand, when the alarm stop signal is determined to be the snooze stop signal ("snooze stop signal" in Step 20), the control unit 21 determines whether the number of times that the snooze stop signals are received from the start of the process exceeds the snooze count set by the user (Step 21). When the number of reception times exceeds the snooze count (Yes in Step 21), the control unit 21 handles the snooze stop signal in the same way as the complete stop signal and terminates the process.

When the number of reception times of the snooze stop signal is equal to or less than the snooze count (No in Step 21), the control unit 21 determines whether the snooze time period elapses or not (Step 22). When the control unit 21 determines that the snooze time period does not elapse (No in Step 22), the control unit 21 determines whether the snooze time period elapses or not again (Step 22).

When the control unit 21 determines that the snooze time period elapses (Yes in Step 22), the control unit 21 generates the alarm output signal and proceeds to Step 14 of causing the notification unit 25 to output the alarm, thereby repeatedly performing the same process.

It should be noted that the control unit 21 may determine whether the basal body temperature data is received from the thermometer 100 or not when a predetermined prediction time period elapses, separately from the flow described above, and in the case where the basal body temperature data is received, the data may be transmitted to the server 300.

As described above, according to this embodiment, it is possible to stop the alarm of the user terminal 200 by the input operation by the user with respect to the thermometer 100. As a result, the user inevitably operates the thermometer 100 along with stopping the alarm at the time of awakening. Thus, it is possible to urge the user to habitually take the basal body temperature and obtain the highly reliable basal body temperature data.

Further, it is possible to provide the alarm function for the user terminal 200 while maintaining the cooperation of the thermometer 100 and the alarm function with each other, which can make the device structure of the thermometer 100 simple. Therefore, it is possible to reduce a burden on the user at the time of the measurement. In addition, by providing the alarm function for the user terminal 200, the alarm function can be further enhanced as compared to the case where the alarm function is provided for thermometer 100. Furthermore, it is also ensure operability at the time of performing various settings.

Further, according to this embodiment, the user terminal 200 has the snooze function. Thus, it is possible to increase certainty of causing the user to wake up and take the body temperature. Further, it is possible to select one of the complete stop and the snooze stop of the alarm by the operation of the thermometer 100. Thus, even in the case where the alarm is temporarily stopped by the snooze function, it is possible to urge the user to take the body temperature.

In addition, the operation reception unit 13 of the thermometer 100 is disposed on the side surface 123 on which the user can hold the thermometer 100. With this structure, after operating the operation reception unit 13, the user can take the body temperature while holding the thermometer 100 without change. Further, the alarm stop operation may also serve as an activation operation of the thermometer 100. Thus, it is possible to urge the user to take the basal body temperature habitually at a regular measurement time after awakening, with the result that the highly reliable basal body temperature data can be obtained.

[Modified Example]

The operation reception unit 13 of the thermometer 100 is not limited to have such a structure as to be disposed on the side surface 123 and may be disposed on the front surface 121 or the back surface 122, for example. Further, in the case where the operation reception unit 13 is constituted of a plurality of operation buttons, an arrangement of the operation buttons is not particularly limited.

Further, the thermometer 100 may have a cap (case) capable of being engaged with the casing 120 and covering all or a part of the casing 120 and the temperature sensing unit 110. In this case, when the cap is detached from the casing 120, the thermometer 100 can be activated, and the alarm stop signal can be output. That is, the thermometer 100 may have the structure without the operation reception unit 13. With this structure, at the time when the alarm is stopped, the user is urged to take the body temperature inevitably, which can contribute to the habitual body temperature measurement. In addition, the cap can keep the temperature sensing unit 110 that is brought into contact with the inside of the oral cavity sanitary.

In the description of the above embodiment, the short distance communication unit 26 of the user terminal 200 has the reception standby state and the reception rejection state, and the control unit 21 of the user terminal 200 controls these states. However, the structure is not limited to this. For example, the short distance communication unit 26 may be connected to the communication unit 16 of the thermometer 100 in a wired manner, for example, and may be in a standby state so as to perform reception constantly.

In the description of the above embodiment, when the basal body temperature prediction time elapses, the measured basal body temperature data can be automatically transmitted to the user terminal 200. However, the structure is not limited to this. For example, the data may be transmitted when the actual measurement time period elapses. Alternatively, after a predetermined time period (for example, approximately 1 to 10 minutes) elapses from when the alarm stop signal is received, the measured basal body temperature data may be transmitted.

In addition, the basal body temperature data is automatically transmitted from the thermometer 100 to the user terminal 200. However, the structure is not limited to this. For example, the data may be manually transmitted by a predetermined input operation by the user. In this case, for example, the operation reception unit 13 of the thermometer 100 may include a data transmission button.

In addition, the contents of the various settings relating to the alarm are not limited to the above. For example, the control unit 21 (setting unit 201) does not perform switching on and off of the snooze mode, and the snooze mode may be set to on in advance. Further, the alarm duration time may be set in advance, or the alarm may be caused to be continuously output until the alarm stop signal is received. Furthermore, the snooze time period and the snooze count may also be set in advance.

In addition, in the description of the above embodiment, the user terminal 200 is the information processing apparatus, but is not limited to this. For example, the user terminal 200 may be an alarm apparatus having an alarm function and a function accompanied therewith or another electronic apparatus.

In addition, the thermometer 100 is not limited to the basal thermometer but may be a normal thermometer for measuring a body temperature during fever or for health management.

<Second Embodiment>

Subsequently, a second embodiment of the present invention will be described. In this embodiment and embodiments subsequent thereto, descriptions on the same structures and functions as the first embodiment will be omitted, and points different from the first embodiment will be described.

This embodiment is different from the first embodiment in that, in the case where the control unit 21 of the user terminal 200 determines that the basal body temperature data is not received when the predetermined measurement time period elapses after receiving the alarm stop signal, the alarm can be output again. With this structure, if the user stops the alarm and then falls asleep without taking the body temperature, it is possible to urge the user to wake up again and take the body temperature.

The structures of the thermometer 100, the user terminal 200, and server 300 are the same as those in the first embodiment, so descriptions thereof will be omitted. Hereinafter, an operation example of the user terminal 200 will be described.

Figure 8:
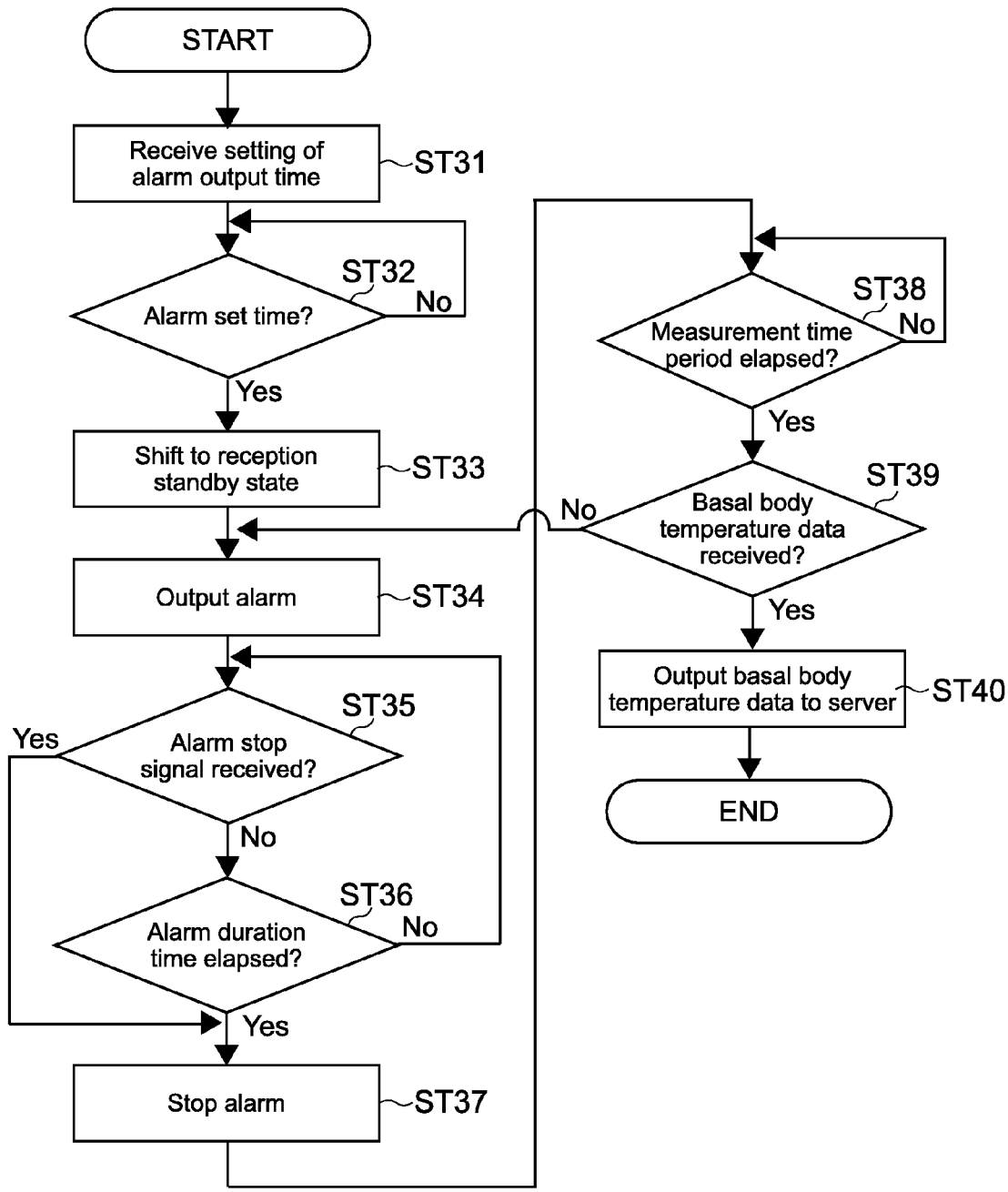
FIG. 8 A flowchart showing an operation flow of the user terminal in a second embodiment of the present invention.

FIG. 8 is a flowchart showing an operation flow in which, in the case where the basal body temperature data is not received after the alarm is stopped at the time of the measurement of the body temperature, the user terminal 200 in this embodiment causes the alarm to be output again. The operation is performed by different hardware and a program (software) in cooperation with each other under the control of the control unit 21 of the user terminal 200. In the following description, for convenience, the control unit 21 of the user terminal 200 is set as a main of the operation, and a description on the same content as the first embodiment will be simplified. Further, in this embodiment, the assumption is made that the snooze function is set to off, but the snooze function may be set to on. In this case, the same operation as the first embodiment is performed.

First, the control unit 21 receives settings of the alarm output time and the like by the user (Step 31).

Then, the control unit 21 determines whether the alarm set time is reached or not (Step 32). When the control unit 21 determines that the set time is not reached (No in Step 32), the control unit 21 determines whether the set time is reached or not again (Step 32).

When the control unit 21 determines that the alarm set time is reached (Yes in Step 32), the control unit 21 causes the short distance communication unit 26 to shift to the reception standby state (Step 33), generates the alarm output signal, and causes the notification unit 25 to output the alarm (step 34).

Then, the control unit 21 determines whether the alarm stop signal is received from the thermometer 100 or not (Step 35). When the control unit 21 determines that the alarm stop signal is not received (No in Step 35), the control unit 21 determines whether the alarm duration time set by the user elapses or not (Step 36). When the control unit 21 determines that the alarm duration time does not elapse (No in Step 36), the control unit 21 determines whether the alarm stop signal is received or not again while continuing the output of the alarm (Step 35). When the control unit 21 determines that the alarm duration time elapses (Yes in Step 36), the control unit 21 stops the alarm (Step 37) and proceeds to Step 38 subsequent thereto.

Further, also in the case where the control unit 21 determines that the alarm stop signal is received (Yes in step 35), the alarm is stopped (Step 37).

Then, the control unit 21 determines whether the predetermined measurement time period elapses or not after the alarm stop signal is received (Step 38). In this operation example, the predetermined measurement time period is set as a predetermined prediction time period. When the prediction time period does not elapse (No in step 38), the control unit 21 determines whether the prediction time period elapses or not again (step 38).

When the control unit 21 determines that the prediction time period elapses (Yes in Step 38), the control unit 21 determines whether the basal body temperature data is received from the thermometer 100 or not (step 39). When the control unit 21 determines that the data is not received (No in Step 39), the control unit 21 proceeds to Step 34 in which the alarm is output and repeatedly perform the process.

On the other hand, When the control unit 21 determines that the basal body temperature data is received (Yes in Step 39), the control unit 21 outputs the basal body temperature data to server 300 via the Internet 50 (Step 40) and then terminates the process.

As described above, according to this embodiment, even if the user falls asleep after stopping the alarm, it is possible to urge the user to wake up and take the body temperature. As a result, it is possible to reliably cause the user to wake up and obtain basal body temperature data. Thus, it is possible to increase the reliability of the basal body temperature data.

[Modified Example]

In the embodiment described above, whether the basal body temperature data is received or not is determined in the case where it is determined that the predetermined measurement time period elapses. However, the process is not limited to this. For example, it is also possible to determine whether the basal body temperature data is received or not in the case where it is determined that a predetermined time period (for example, approximately 1 to 10 minutes) elapses after the prediction time period elapses from when the alarm stop signal is received. With this operation, it is also possible to obtain the same effect as the above embodiment.

Further, in the above embodiment, the description is given in which the predetermined measurement time period is the prediction time period but may be an actual measurement time period.

<Third Embodiment>

Subsequently, a third embodiment of the present invention will be described.

This embodiment is different from the above embodiments in that on the basis of the change over time in the body temperature measurement value, the control unit 21 determines whether the user falls asleep or not during the body temperature measurement, and when the control unit 21 determines that the user falls asleep, the control unit 21 can cause the alarm to be output. With this structure, it is possible to prevent the user from falling asleep during the body temperature measurement.

Further, in this embodiment, the short distance communication unit 26 can receive data relating to the change over time in the body temperature measurement value from the thermometer 100. For example, the data may be received simultaneously with the basal body temperature data or may be received individually.

Specifically, the control unit 21 can determine that the user falls asleep during the body temperature measurement, when the measurement value is continuously increased during a time period from the elapse of the prediction time period to the actual measurement time period.

A general user takes the body temperature by the prediction body temperature check by which the measurement is terminated for a short time period (for example, approximately several tens of seconds). Therefore, after the prediction body temperature check, the temperature sensing unit 110 of the thermometer 100 is released from the body, and a measurement value obtained decreases. On the other hand, if the measurement value continues to increase after the elapse of the prediction time period, the user continues to take the body temperature after the elapse of the prediction time period and may probably be asleep, so the above determination is conducted.

Further, in this embodiment, in consideration of the fact that some users take the body temperatures by the actual measurement body temperature check, it is also possible to switch on and off of the mode for performing notification of urging the user to wake up (going-back-to-sleep prevention mode).

As described above, according to this embodiment, it is possible to prevent the user from going back to sleep during the body temperature measurement. As a result, it is possible to suppress consumption of a battery of the thermometer 100 and urge the user to wake up. Thus, it is possible to increase the convenience of the user and urge the user to habitually take the body temperature.

[Modified Example]

In the description of the above embodiments, the determination whether the user falls asleep or not is performed on the basis of the change over time in the body temperature measurement value but is not limited to this. For example, the determination whether the user falls asleep or not may be performed by outputting radio waves of a predetermined frequency to the user, receiving reflected radio waves, and thus measuring a sleep condition. Alternatively, the determination may be performed by measuring brain waves or the like. Such a function that the sleep condition is measured may be entirely or partially provided for the user terminal 200 or may be provided for another apparatus.

Further, in the above embodiments, the determination whether the user falls asleep or not may be performed by the control unit 11 of the thermometer 100, and a result of the determination may be output to the user terminal 200. As a result, the user terminal 200 can output the alarm upon reception of the determination result indicating that the user falls asleep.

Alternatively, not the user terminal 200 but the thermometer 100 may urge the user to wake up. Specifically, in the case where it is determined that the user falls asleep, the thermometer 100 may output beeps or the like for urging the user to wake up from the notification unit 15. With this structure, it is also possible to prevent the user from falling asleep during the body temperature measurement.

<Fourth Embodiment>

Subsequently, a fourth embodiment of the present invention will be described.

The user terminal 200 according to this embodiment is the electronic apparatus having the alarm function as in the first embodiment but is different from the first embodiment in that, during the body temperature measurement, out of a plurality of presentation patterns of a predetermined content, a predetermined presentation pattern is selected and reproduced.

The predetermined content is not particularly limited, but it is possible to use a content of choice for women, which is periodically distributed. In the following description, a fortune-telling content is given as an example.

Further, as a method of selecting the predetermined presentation pattern, a presentation pattern corresponding to the basal body temperature data of the user can be selected on the basis of the result of the basal body temperature analysis data processed by the server 300.

As in the first embodiment, the server 300 can provide the body temperature management application to the user terminal 200, perform an analysis process of the basal body temperature data received from the user terminal 200, and transmit a graph, an advice, a body condition, a psychological condition, or the like of the user as the analysis result to the user terminal 200.

As in the first embodiment, the storage unit 34 of the server 300 stores the basal body temperature data of each user which is transmitted from the user terminal 200 and stores the analysis data that indicates the analysis result of the basal body temperature data of each user. Further, these pieces of data are associated with the user IDs, for example, and stored for each user.

The control unit 31 (CPU 311) of the server 300 performs the analysis process for the basal body temperature data. Specifically, from the obtained basal body temperature data, the next ovulation prediction date and menstruation start prediction date are calculated, and on the basis of these calculation results, predetermined periods are sectioned for each typical body condition and psychological condition of the user. The period to be sectioned is not limited to the period during which the basal body temperature data is already obtained and can be a period during which the ovulation prediction date, the menstruation start prediction date, or the like can be predicted.

Further, in the following description, the periods sectioned are referred to as "sectioned periods".

Then, the control unit 31 generates analysis data that indicates the analysis results of the menstruation start prediction date, the ovulation prediction date, the sectioned periods, and the like. The analysis data may be provided by indicating the analysis results on a calendar or a graph.

As a result, the body and psychological conditions of the user are easily grasped and predicted, and displaying of the content, an advice, or the like based on the body condition and the psychological condition is easily provided.

These analysis results are uploaded to the user terminal 200 via the Internet 50 and stored in the storage unit 24 of the user terminal 200. As a result, the user terminal 200 can reproduce the received basal body temperature analysis data through the display unit 22.

Figure 9:
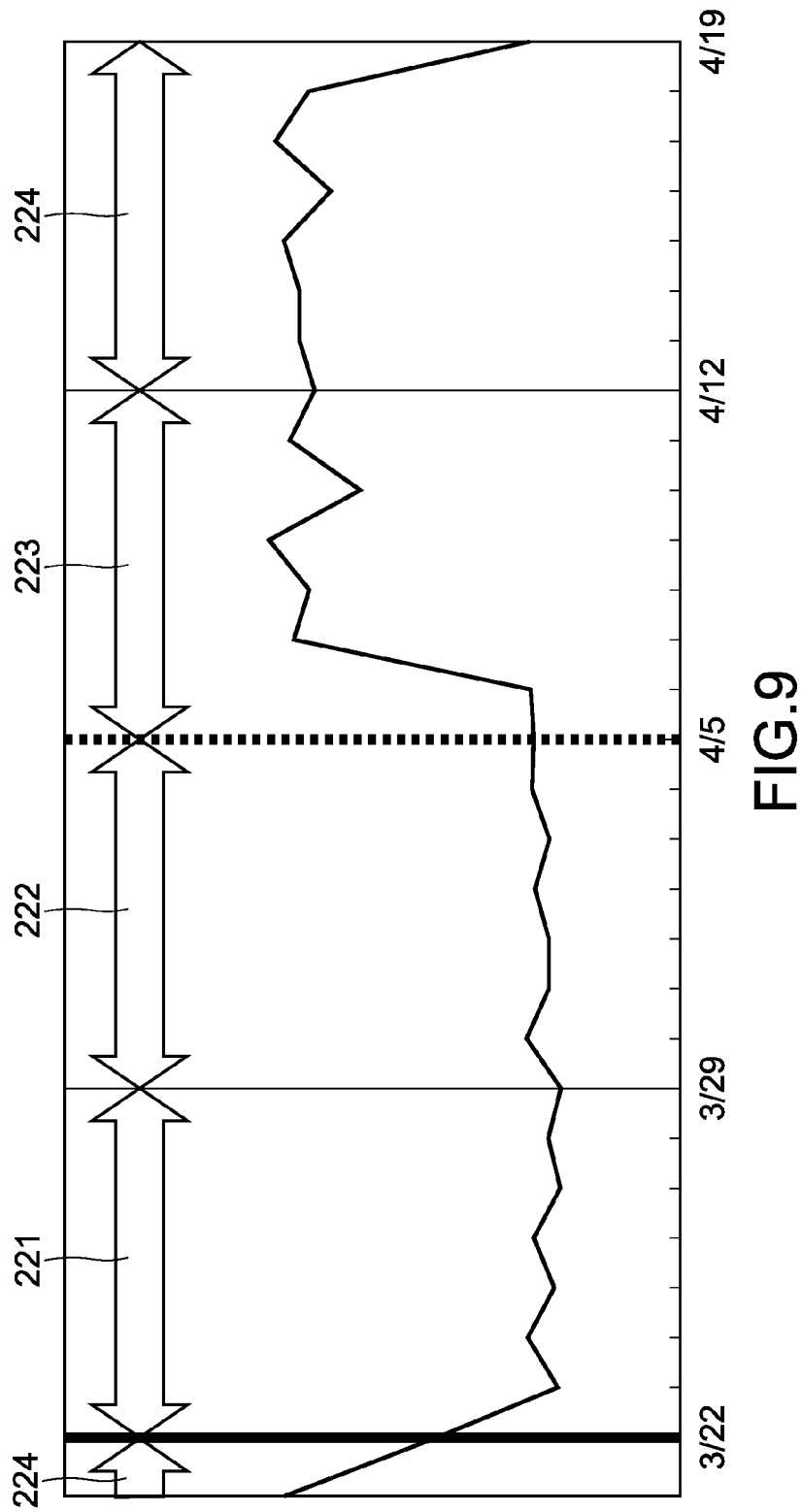
FIG. 9 An analysis data image example of basal body temperatures on a display unit of the user terminal in a fourth embodiment of the present invention.

FIG. 9 shows an example of an analysis data image of the basal body temperature displayed on the display unit 22 of the user terminal 200 and shows a graph that indicates changes in the basal body temperature value on a daily basis. Further, a lateral axis of the graph in FIG. 9 indicates dates, and a vertical axis of the graph indicates the basal body temperature values. In addition, a thick solid line indicates the menstruation start date, and a thick broken line indicates the ovulation prediction date. With reference to the graph, an outline of the changes in the basal body temperature value on the daily basis and the sectioned periods decided by the server 300 (control unit 31) will be described.

As shown in FIG. 9, generally, the basal body temperature data has an approximately 28-day periodicity from a certain menstruation start date to the next menstruation start date. Further, the data shows a biphasic form. A phase from a menstruation start date to an ovulation date corresponds to a low-temperature phase, and a phase from the ovulation date to the next menstruation start date corresponds to a high-temperature phase. Such a periodical change in the basal body temperature value is based on periodicity of hormone secretion. That is, by grasping the change in the basal body temperature value on the daily basis, it is possible to grasp the body condition, the psychological condition, and the like based on the hormone secretion condition.

Further, by obtaining the basal body temperature data for several or longer periods, it is possible to predict the body condition and the psychological condition even on a day when the basal body temperature value is not obtained.

FIG. 9 shows an example of the sectioned periods. For example, the periods can be set as follows. A first period 221 corresponds to a menstruation period of predetermined days (for example, 7 days) from the menstruation start date, a second period 222 correspond to a period after the lapse of the first period 221 to a preceding day of the ovulation prediction date, a third period 223 corresponds to a period of predetermined days (for example, 7 days) from the ovulation prediction date, and a fourth period 224 corresponds to a period after the lapse of the third period 223 to a preceding day of the menstruation start date. General body conditions and psychological conditions of the periods are as follows. That is, during the first period 221, the body and psychological conditions are bad due to menstrual cramps. During the second period 222, the body and psychological conditions are stable and good. During the third period 223, the body and psychological conditions turn into an unstable tendency. During the fourth period 224, the unstable tendency is accelerated.

It should be noted that the sectioned periods are not limited to the above. For example, in addition to the above periods, a fifth period that indicates a period during which a possibility of pregnancy is high may be set. Alternatively, the sectioned periods may set to two periods of the low-temperature phase and the high-temperature phase.

The sectioned periods may be presented through the display unit 22 as shown in FIG. 9. This enables the user to grasp the body condition and the psychological condition. Further, for example, only a part such as the second period which is the good-condition period may be presented or not.

In the storage unit 24 of the user terminal 200, a plurality of presentation patterns of a fortune-telling content are stored with the patterns associated with the periods described above. FIG. 10 shows an example of a database of the presentation patterns stored in the storage unit 24. For example, if fortune-telling results A and B are provided, the presentation patterns corresponding to the psychological conditions during the first to fourth periods are stored for each result. For example, four presentation patterns of A-1, A-2, A-3, and A-4 are corresponded to the result A. All the presentation patterns stored in the storage unit 24 may be downloaded from the server 300 via the Internet 50.

Further, as presentation patterns corresponding to the psychological condition, for example, in the case where the fortune-telling result A on the measurement date shows a good fortune, when the sectioned period is the second period during which the condition is good, a comment of urging a positive action is indicated, and when the sectioned period is the fourth period during which the condition is bad, a commend with less active representation in consideration of the psychological condition of the user. That is, it is possible to avoid presentation of a content unacceptable by the user during the bad-condition period, which can suppress making the user unpleasant.

During the measurement of the body temperature, the control unit 21 selects the fortune-telling result on the measurement date on the basis of a registered birthday or the like of the user, selects the presentation pattern corresponding to the sectioned period to which the measurement date is predicted to belong, and outputs the presentation pattern to the display unit 22. As a result, it is possible to present the fortune-telling result based on the selected presentation pattern to the user during or after the measurement of the body temperature.

Hereinafter, an operation example of the user terminal 200 will be described.

Figure 11:
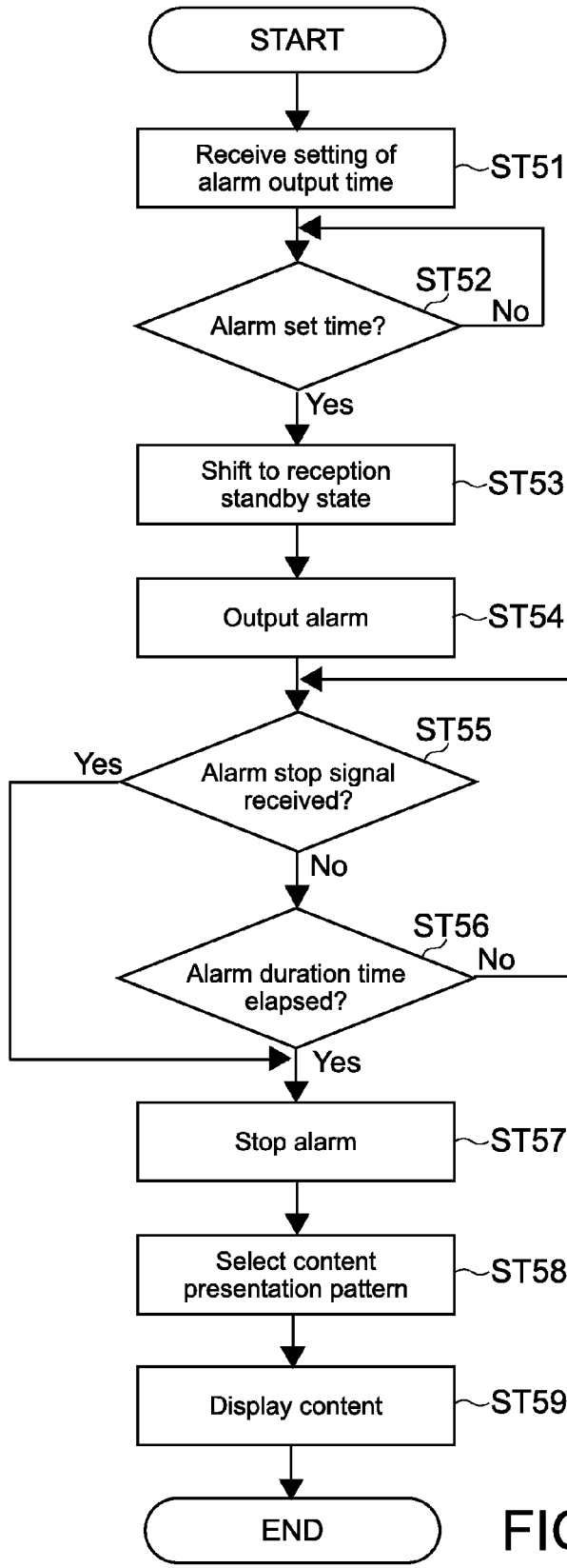
FIG. 11 A flowchart showing an operation flow of the user terminal in the fourth embodiment of the present invention.

FIG. 11 is a flowchart showing an operation flow of stopping the alarm and presenting the content by the user terminal 200 in this embodiment at the time of measurement of the body temperature. The operation is performed by different hardware and a program (software) in cooperation with each other under the control of the control unit 21 of the user terminal 200. In the following description, for convenience, the control unit 21 of the user terminal 200 is set as a main of the operation, and a description on the same content as the first embodiment will be simplified. Further, in this embodiment, the assumption is made that the snooze function is set to off, but the snooze function may be set to on. In this case, the same operation as the first embodiment is performed.

First, the control unit 21 receives a setting of an alarm output time or the like by the user (Step 51).

Then, the control unit 21 determines whether the alarm set time is reached or not (Step 52). When the control unit 21 determines that the set time is not reached (No in Step 52), the control unit 21 determines whether the set time is reached or not again (Step 52).

When the control unit 21 determines that the alarm set time is reached (Yes in Step 52), the control unit 21 causes the short distance communication unit 26 to shift to the reception standby state (Step 53), generates the alarm output signal, and causes the notification unit 25 to output the alarm (step 54).

Then, the control unit 21 determines whether the alarm stop signal is received from the thermometer 100 or not (Step 55). When the control unit 21 determines that the signal is not received (No in Step 55), the control unit 21 determines whether the alarm duration time set by the user elapses or not (Step 56). When the control unit 21 determines that the alarm duration time does not elapse (No in Step 56), the control unit 21 determines whether the alarm stop signal is received or not while continuing the output of the alarm (Step 55). When the control unit 21 determines that the alarm duration time elapses (Yes in Step 56), the control unit 21 causes the alarm to be stopped (Step 57).

Further, when the control unit 21 determines that the alarm stop signal is received (Yes in Step 55), the control unit 21 also stops the alarm (Step 57).

Then, the control unit 21 selects the presentation pattern of the content (Step 58). For the presentation pattern, the content corresponding to the psychological condition of the user, which is predicted on a day when the process is performed (hereinafter, referred to as measurement date) on the basis of the basal body temperature data. For example, on the measurement date, when it is predicted that the user is in the second period, and the fortune-telling result is A, the presentation pattern of A-2 is selected. Further, the prediction of the psychological condition can be performed on the basis of periodicity of the basal body temperature data obtained up until the preceding day.

The control unit 21 outputs the content with the selected presentation pattern to the display unit 22 (Step 59) and terminates the process.

It should be noted that, separately from the flow described above, the control unit 21 determines whether the basal body temperature data is received from the thermometer 100 at the time when the predetermined prediction time period (or actual measurement time period) elapses, and when the basal body temperature data is received, the control unit 21 transmits the data to the server 300.

As described above, according to this embodiment, during or immediately after the basal body temperature measurement, it is possible to present the content corresponding to the body condition and the psychological condition of the user. As a result, it is possible to provide enjoyment to the user at the time of the measurement and motivate the user to continue the measurement. In addition, it is possible to prevent the user from going back to sleep after the measurement.

In addition, the content is selected on the basis of the psychological condition of the user. Therefore, it is possible to suppress making the user unpleasant and urge the user to continuously subscribe the content. As a result, it is possible to further increase the effect obtained by reproducing the content.

In addition, when the predetermined measurement time period elapses, the basal body temperature data is automatically transmitted to the user terminal 200 from the thermometer 100. As a result, it is possible to save the user the trouble of transmitting the basal body temperature data, which can enhance the convenience of the user. In addition, the user terminal 200 can update the basal body temperature data managed by the server 300 immediately after the measurement. Thus, the server 300 can use latest basal body temperature data to predict the body condition and the psychological condition, with the result that a more appropriate content can be provided.

[Modified Example]

It is possible to periodically distribute the contents from the server 300 to the user terminal 200. For example, the server 300 can select the fortune-telling result on the measurement date for each user and distribute the plurality of presentation patterns corresponding to the results every day. As a result, a content of data which has to be stored in the storage unit 24 of the user terminal 200 can be reduced, and various contents can be presented for the user.

In addition, the selection process of the presentation pattern of the content may be performed not by the user terminal 200 but by the server 300. In this case, a database of the presentation patterns of the contents is not stored in the storage unit 24 of the user terminal 200 but may be stored only in the server 300. That is, the server 300 may select the content on the basis of the basal body temperature data received from the user terminal 200 at the time when the alarm is stopped and distribute the content to the user terminal 200 to cause the content to be reproduced.

Further, the content may include an advice related to health or beauty. As a result, the user can obtain the advice corresponding to the body condition or the psychological condition based on the basal body temperature data.

Furthermore, the content does not have to be reproduced during or immediately after the measurement. For example, at a time corresponding to a user's activity after the measurement, a predetermined content may be presented. Specifically, it is possible to present an advice related to lunch at about 11 a.m. before lunch.

In addition, the content to be reproduced is not only displayed on the display unit 22 but may be output from a speaker (notification unit 25) as voice data.

In addition, the present invention is not limited to the above embodiments and can be variously modified without departing from the gist of the present disclosure. Further, the first to fourth embodiments described above can be combined in any way and implemented as long as a contradiction does not arise.

DESCRIPTION OF REFERENCE NUMERALS 1 body temperature management system
100 thermometer
11 control unit
13 operation reception unit
16 communication unit
120 casing
121 front surface
122 back surface
123 side surface
200 user terminal (electronic apparatus)
21 control unit
24 storage unit
25 notification unit (alarm unit)
26 short distance communication unit (reception unit)

The invention claimed is:

1. An electronic apparatus, comprising:
an alarm circuit capable of outputting an alarm;
a reception circuit that receives an alarm stop signal by a wireless communication or wired communication from a thermometer which is an external device; and
a control circuit that causes the alarm circuit to output the alarm at a set time and stop the alarm on the basis of the alarm stop signal,
wherein
the alarm stop signal received by reception circuit comprises a first alarm stop signal and a second alarm stop signal, and
when the reception circuit receives the first alarm stop signal, the control circuit causes the alarm of the alarm circuit to be completely stopped, and when the reception circuit receives the second alarm stop signal, the control circuit causes the alarm to be temporarily stopped in such a manner that the alarm of the alarm circuit is caused to be output again after a lapse of a predetermined time period.

2. The electronic apparatus according to claim 1, wherein
the reception circuit has a first state in which the alarm stop signal is capable of being received and a second state in which a reception of the alarm stop signal is rejected, and
the control circuit causes the reception circuit to shift from the second state to the first state at the set time.

3. The electronic apparatus according to claim 1, wherein after receiving the alarm stop signal, the reception circuit receives basal body temperature data output from the thermometer when a predetermined measurement time period of the thermometer elapses.

4. The electronic apparatus according to claim 3, wherein
in the case where the control circuit determines that the basal body temperature data is not received when the predetermined measurement time period elapses after receiving the alarm stop signal, the control circuit causes the alarm to be output again.

5. The electronic apparatus according to claim 3, further comprising
a storage circuit that stores a plurality of presentation patterns of a predetermined content, wherein
the control circuit selects and reproduces the presentation pattern corresponding to the received basal body temperature data from among the plurality of presentation patterns of the predetermined content.

6. An electronic apparatus, comprising:
an alarm circuit capable of outputting an alarm;
a reception circuit that receives an alarm stop signal by a wireless communication or wired communication from a thermometer which is an external device; and
a control circuit that causes the alarm circuit to output the alarm at a set time and stop the alarm on the basis of the alarm stop signal, wherein
the reception circuit is capable of receiving data relating to a change over time in body temperature measurement value from the thermometer, and
the control circuit determines whether a user falls asleep or not during a body temperature measurement on the basis of the change over time in the body temperature measurement value received, and in the case where the control circuit determines that the user falls asleep, the control circuit causes the alarm to be output.

7. A thermometer, comprising
a communication circuit that transmits a signal by a wireless communication or wired communication to an electronic apparatus which is an external device for stopping an alarm of the electronic apparatus having an alarm function; and
a control circuit that generates a first alarm stop signal for completely stopping the alarm on a basis of a first input operation and that generates a second alarm stop signal for temporarily stopping the alarm in such a manner that the alarm is generated again after a lapse of a predetermined time period on a basis of a second input operation.

8. The thermometer according to claim 7, further comprising:
an operation reception circuit that receives the first and the second input operations.

9. The thermometer according to claim 8, wherein when the signal is generated, a measurement of a body temperature is started.

10. The thermometer according to claim 8, further comprising
a casing having a front surface, a back surface, and a side surface, the front surface including a display circuit on which a body temperature value measured is displayed, the back surface being opposed to the front surface, the side surface being continuously connected with the front surface and the back surface and capable of being held by the user during the measurement of the body temperature, wherein
the operation reception circuit is disposed on the side surface.

11. The thermometer according to claim 7, wherein the communication circuit is capable of outputting measured basal body temperature data when a predetermined measurement time period elapses.

12. A body temperature management system, comprising:
a thermometer capable outputting an alarm stop signal; and
an electronic apparatus, which is external to the thermometer, including an alarm circuit capable of outputting an alarm, a reception circuit that receives the alarm stop signal from the thermometer by a wireless communication or wired communication, and a control circuit that causes the alarm circuit to output the alarm at a set time and stop the alarm on the basis of the alarm stop signal,
wherein
the alarm stop signal received by reception circuit comprises a first alarm stop signal and a second alarm stop signal, and
when the reception circuit receives the first alarm stop signal, the control circuit causes the alarm of the alarm circuit to be completely stopped, and when the reception circuit receives the second alarm stop signal, the control circuit causes the alarm to be temporarily stopped in such a manner that the alarm of the alarm circuit is caused to be output again after a lapse of a predetermined time period.

13. An alarm control method, comprising:
causing an alarm for urging a user to wake up to be output at a set time;
receiving an alarm stop signal by a wireless communication or wired communication from a thermometer, which is an external device, that measures a body temperature of the user and is capable of outputting the alarm stop signal; and
causing the alarm to be stopped on the basis of the alarm stop signal received from the thermometer,
wherein
the alarm stop signal received by reception circuit comprises a first alarm stop signal and a second alarm stop signal, and
when the first alarm stop signal is received, causing the alarm to be completely stopped, and when the second alarm stop signal is received, causing the alarm to be temporarily stopped in such a manner that the alarm is caused to be output again after a lapse of a predetermined time period.

* * * * *